United States Patent [19]

Gregory et al.

[11] Patent Number: 4,665,220

[45] Date of Patent: May 12, 1987

[54] USE OF STABILIZED PILLARED INTERLAYERED CLAYS AS CATALYSTS IN REACTIONS CAPABLE OF CATALYSIS BY PROTONS

[75] Inventors: Reginald Gregory; David J. Westlake, both of Surrey, England

[73] Assignee: The British Petroleum Company, p.l.c., London, England

[21] Appl. No.: 720,795

[22] Filed: Apr. 8, 1985

Related U.S. Application Data

[62] Division of Ser. No. 455,520, Jan. 4, 1983, Pat. No. 4,542,250.

[30] Foreign Application Priority Data

Jan. 9, 1982 [GB] United Kingdom ............... 8200633

[51] Int. Cl.$^4$ ............................................. C07C 67/04

[52] U.S. Cl. ...................................... 560/247; 560/84; 560/96

[58] Field of Search ........................... 560/247, 84, 96

[56] References Cited

U.S. PATENT DOCUMENTS 4,440,958  4/1984  Gregory .............................. 560/247
4,465,852  8/1984  Sato .................................... 560/247

FOREIGN PATENT DOCUMENTS 31687  7/1981  European Pat. Off. ............ 560/247

Primary Examiner—Michael L. Shippen
Attorney, Agent, or Firm—Brooks Haidt Haffner & Delahunty

[57] ABSTRACT

A method for carrying out processes capable of catalysis by protons using as catalyst a stabilized pillared interlayered clay.

5 Claims, No Drawings

USE OF STABILIZED PILLARED INTERLAYERED CLAYS AS CATALYSTS IN REACTIONS CAPABLE OF CATALYSIS BY PROTONS

This is a division of application Ser. No. 455,520 filed Jan. 4, 1983, now U.S. Pat. No. 4,542,250.

The present invention relates generally to processes capable of being catalysed by protons and in particular to such processes in which the catalyst is a cation-exchangeable solid material.

Natural and synthetic clays having a lamellar structure with interlamellar spaces disposed between the lamellar layers are well known. Smectites, such as bentonite, montmorillonites and chlorites are a class of clays possessing such a lamellar structure. Montmorillonite has an idealised stoichiometric composition corresponding to $Na_{0.67}Al_{3.33}Mg_{0.67}(Si_8)O_{20}(OH)_4$. Structurally, it comprises a central layer containing octrahedrally coordinated aluminium and magnesium in the form of their oxides and hydroxides sandwiched between two layers containing tetrahedrally coordinated silicon essentially in the form of its oxide. Normally in nature cations are present to compensate for the change imbalance caused by isomorphous substitution of $Mg^{2+}$ for $Al^{3+}$ in the octahedral layer, and/or $Al^{3+}$ or other ions for $Si^{4+}$ in the tetrahedral layers. The octrahedral and tetrahedral regions are tightly bound together to form a lamellar layer. The space between these lamellar layers, ie the interlamellar space, in natural clays is normally occupied by exchangeable $Ca^{2+}$ or $Na^+$ ions. The distance between the interlamellar layers can be substantially increased by absorption of a variety of polar molecules such as water, ethylene glycol, amines etc., which enter the interlamellar space and in doing so push apart the lamellar layers. The interlamellar spaces tend to collapse when the molecules occupying the space are removed, for example by heating the clay at a high temperature.

Our European patent publications Nos. 0031252 and 0031687 describe the use of cation-exchangeable layered clays in proton-catalysed reactions eg the hydration of olefins to form alcohols, and esterification, either of the type whereby an acid is reacted with an alcohol to form the ester or the type whereby an olefin is reacted with a carboxylic acid to form the ester.

Also known from U.S. Pat. Nos. 4,216,188 and 4,248,739 are stablised pillared interlayered clays in which the layers are separated and supported by "pillars" of monomeric, oligomeric or polymeric species derived from metal hydroxides. Such clays can inherently possess a higher degree of thermal stability and improved hydrothermal stability when compared with non-pillared layered clays. In U.S. Pat. Nos. 4,248,739 the use of the pillared interlayered clays as sorbents, catalysts and catalytic supports is described. The clays are said to be useful as hydrocarbon conversion catalysts for use in conventional catalytic cracking, hydrocracking, hydrotreating, isomerisation and reforming processes. Similar uses are described for the pillared clays of U.S. Pat. No. 4,216,188 and this specification in Example 6 describes the esterification of n-butanol with propionic acid.

We have now found that stabilised pillared interlayered clays can catalyse other reactions capable of being catalysed by protons and in doing so they can offer certain advantages over non-pillared layered clays in that, for example, they can be exposed to higher temperatures without destroying their layered structure.

Accordingly, the present invention provides a method for carrying out a process capable of catalysis by protons using as catalyst a cation-exchangeable solid material characterised in that the cation-exchangeable solid material is a stabilised pillared interlayered clay and the process capable of catalysis by protons is either:

(i) a process for the production of an ether by reacting either an olefin or an olefin oxide with an alcohol, or (ii) a process for the production of an ether by reacting either a primary or secondary aliphatic alcohol, a polyol or an olefin oxide, or (iii) a process for the production of an alkyl aromatic compound by reacting an aromatic compound with either an alcohol or an olefin, or (iv) a process for the production of an alcohol by reacting an olefin with water, or (v) a process for the production of an ester by reacting either an olefin or an olefin oxide with a carboxylic acid.

Suitable stabilised pillared interlayered clays which may be used in the invention and methods for making them are described in the specifications of U.S. Pat. Nos. 4,216,188 and 4,248,739. Typically, the pillared clay may be prepared by reacting a colloidal solution of a mono-ionic montmorillonite having a concentration of 100 mg to 800 mg montmorillonite per liter, in the form of fully dispersed negatively charged unit layers at room temperature with an aged sol of a metal hydroxide aged for at least 5 days at ambient temperature, said metal hydroxide being selected from the group consisting of aluminium hydroxide and chromium hydroxide, at a pH adjusted below the zero charge point having a residual net positive charge on the said metal hydroxide, under vigorous agitation, resulting in a rapid flocculation of the montmorillonite cross-linked with said metal hydroxide, separating the product from the liquid phase, and stabilising the product by heat treatment. Further details of this process may be found in U.S. Pat. No. 4,216,188. Alternatively, the pillared clay may suitably be prepared by reacting a smectite-type clay, such as bentonite, with an aqueous solution of a polymeric cationic hydroxy inorganic metal complex, such as chlorhydrol. Further details of this method may be found in U.S. Pat. No. 4,248,739.

The stabilised pillared interlayered clays may suitably be modified and the catalytic activity improved by cation-exchange following treatment with a base, such as ammonia. The nature of this process is described in GB patent application No. 2059408A for example, to which the reader is referred for further details.

Alternatively, the catalyst may be a stabilised pillared interlayered clay in which the pillars are formed after exchanging the natural cations of the clay with more suitable cations. The preparation of stabilised pillared interlayered clays according to this procedure is described in, for example, U.S. Pat. No. 4,238,364.

The stabilised pillared interlayered clay may be used alone or admixed with inorganic oxide matrix components such as silica, alumina, silica-alumina, hydrogels and clays.

The stabilised pillared interlayered clay may be any suitable size or shape as to ensure good contact with the reactants. Suitably, particles or pellets may be employed.

In a particular aspect the invention provides a process for the production of an ether which process comprises reacting an alcohol with either an olefin or an olefin oxide under reaction conditions which result in the formation of an ether in the presence of a stabilised pillared interlayered clay as catalyst.

Suitably, the alcohol may be an aliphatic, cycloaliphatic or aromatic alcohol, which may be mono-, di- or polyhydric. Examples of suitable aliphatic alcohols include methanol, ethanol, propanols, butanols, pentanols and hexanols. An example of a suitable cycloaliphatic alcohol is cyclohexanol and an example of an aryl alcohol is phenol. Diols, such as ethylene glycol and propylene glycol and polyols, such as glycerol may be used. Mixtures of alcohols and/or diols may be employed if desired.

With regard to the olefin or olefin oxide any suitable olefin or olefin oxide may be employed. Suitable olefins include ethylene, propylene, butenes, pentenes and hexenes, diolefins such as butadiene and pentadiene and cyclic olefins such as cyclohexene and cyclopentadiene. Preferably the olefin is a $C_3$ to $C_6$ linear or branched olefin. Mixtures of olefins such as those commonly obtained from refinery streams, such as those derived from the catalytic cracking of hydrocarbons, eg cat-cracked spirit, may also be used if so desired. Suitable olefin oxides include ethylene oxide and propylene oxide. The amount of olefin or olefin oxide employed may be greater or less than the stoichiometric amount required to react completely with the alcohol. Generally, using an olefin oxide, it is preferred to employ a stoichiometric excess of the alcohol in order to maximize the yield of desired ether. Preferably the excess of alcohol to olefin oxide is from 5:1 to 15:1 (molar).

In preferred embodiments of this aspect of the invention mono-, di- and tri-ethylene glycol mono alkyl ethers are produced by reacting ethylene oxide with an alkanol. Thus, for example mono-, di- and tri-ethylene glycol mono-methyl, -ethyl or-butyl ethers, are produced by reacting ethylene oxide with methanol, ethanol or butanol respectively; mono-, di- and tri-propylene glycol monoalkyl ethers are produced by reacting propylene oxide with an alkanol; methyl tertiary butyl ether is produced by reacting methanol with isobutene and 2-methoxybutane is produced by reacting methanol with linear butenes.

The process may be carried out in the liquid phase or in the vapour phase, preferably in the liquid phase. Reaction conditions which result in the formation of an ether will depend on whether the process is carried out in the liquid or the vapour phase and to some extent on the nature of the reactants.

In the liquid phase the pressure is suitably that pressure which maintains a liquid phase at the reaction temperature. In the case of olefins and olefin oxides with suitably high boiling points, eg hexene-1, the reaction may for example be conveniently carried out at the reflux temperature of the reactants and under atmospheric pressure, or at higher temperatures and pressures if so desired. Generally, for olefins the temperature may be up to 300° C., preferably 50° to 250° C. The particular temperature employed within the aforesaid ranges will depend upon the nature of the olefin. For example the temperatures employed for linear olefins will be higher than those employed for the corresponding branched olefins. Using alkylene oxides it is preferred to employ generally lower temperatures, which may suitably be in the range from room temperature to 200° C., preferably from 20° to 160° C.

Solvents may be employed if so desired. Suitable solvents include hydrocarbons, eg alkanes such as hexane and octane. A preferred solvent is sulpholane.

The process may be carried out batchwise or continuously, preferably continuously.

In another aspect the invention also provides a process for the production of ethers by reacting at elevated temperature a primary or secondary aliphatic alcohol or a polyol or an olefin oxide in the presence of a stabilised pillared interlayered clay.

With regard to the primary aliphatic alcohol reactant suitable alcohols include methanol, ethanol, propan-1-ol, butan-1-ol, pentan-1-ol, hexan-1-ol, heptan-1-ol and octan-1-ol. The principal ether in the product resulting from the reaction of a primary aliphatic alcohol in the presence of the lamellar clays is the corresponding 1,1-ether, though the corresponding 1,2-ether, may also be formed. Alkenes and alkene dimers may also be formed. Generally the proportion of alkene in the product increases as the carbon number of the reactant alcohol increases.

With regard to the secondary aliphatic alcohol reactant, suitable alcohols include straight-chain alcohols such as propan-2-ol, butan-2ol, pentan-2-ol, pentan-3-ol, hexan-2-ol and hexan-3-ol and cyclohexanol, of which propan-2-ol and butan-2-ol are preferred. The ethers predominating in the product resulting from the reaction of alkan-2-ol and alkan-3-ols are the 2,2- and 3,3-ethers respectively. Alkenes and alkene dimers are also formed.

The reactant may also be a polyol such as an alkylene glycol. A suitable alkylene glycol is ethylene glycol which produces a mixture of dioxan, and ethylene glycol oligomers (di-ethylene glycol etc). A preferred alkylene glycol is diethylene glycol which produces dioxan in high conversions in the presence of the stabilised pillared interlayered clay. Additionally mixtures of alcohols and/or polyols may be used if so desired.

Suitable olefin oxides which may be used include ethylene oxide and propylene oxide. Thus, for example, reaction of ethylene oxide yields 1,4-dioxan and 2-methyl-1, 3-dioxan and the products from the reaction of propylene oxide include 2,5-dimethyl-1, 3-dioxan. Other olefin oxides yield cyclic ethers, but alpha, beta-unsaturated aldehydes may also be formed. The proportion of unsaturated aldehyde generally tends to increase with the carbon number of the epoxide.

Using an aliphatic alcohol or a polyol, the elevated temperature may suitably be in the range 50° to 300° C., preferably from 150° to 225° C. Employing an olefin oxide as the reactant, the temperature may suitably be in the range 15° to 200° C., preferably 80° to 200° C.

The process may be carried out in the liquid phase or the vapour phase, preferably in the liquid phase.

In a further aspect, the invention provides a process for the production of an alkyl aromatic compound by reacting at elevated temperature an aromatic hydrocarbon with an alkylating agent selected from olefins and $C_2$ or higher alcohols in the presence as catalyst of a stabilised pillared interlayered clay.

The aromatic hydrocarbon may suitably be benzene, naphthalene or other polycyclic aromatic hydrocarbon. Aromatic hydrocarbons substituted by alkyl or other functional groups, such as for example, hydroxyl, alkoxy and hydroxyalkyl, may also be employed. Preferably the aromatic hydrocarbon is benzene or toluene. Mixtures of aromatic hydrocarbons including those derived from steam or catalytic cracking of hydrocarbons, eg steam cracked or cat-cracked spirit, may also be employed if so desired.

The olefin may suitably be a mono-olefin or a diolefin. Suitable mono-olefins include ethylene, propylene and butylenes, though higher olefins, such as for example propylene tetramer, may be employed. Mixtures of olefins such as those derived from steam or catalytic cracking of hydrocarbons, eg steam cracked or cat-cracked spirits may also be employed if so desired. A suitable diolefin is butadiene.

Examples of suitable $C_2$ or higher alcohols which may be employed include ethanol, n-propanol, isopropanol and butanols.

The reaction may be carried out in the presence of a solvent or diluent. Suitable solvents and diluents include hydrocarbons such as alkanes and mixtures of hydrocarbons such as those present, in addition to aromatic compounds and olefins, in fractions derived from steam or catalytic cracking of hydrocarbons.

In a preferred embodiment of this aspect of the invention benzene is reacted with propylene to produce isopropylbenzene (cumene). In another preferred embodiment benzene is reacted with ethylene to produce ethylbenzene. In a further preferred embodiment phenol is reacted with an alkylating agent to produce alkylphenols.

Reaction of an aromatic hydrocarbon with an alkylating agent may suitably be effected in the liquid phase or in the vapour phase. Generally, reaction of an aromatic hydrocarbon with an olefin may be carried out in the liquid phase at a temperature up to 400° C., preferably in the range 100° to 300° C. and at an elevated pressure sufficient to maintain a liquid phase.

The process may be operated batchwise or continuously, preferably continuously.

Typically, under continuous flow conditions, benzene may be alkylated with propylene at a temperature up to 400° C., preferably from 100° to 300° C., at atmospheric or elevated pressure, preferably from 20 to 50 bar. The molar ratio of benzene to propylene may be in the range from about 0.1:1 to 100:1, preferably from 2:1 to 15:1. The ratio of catalyst volume to the liquid feed volume flow rate (residence time) may be up to 5 hours and is preferably in the range from 1 minute to 2 hours. The conditions may be permutated either to maximise desirable products such as cumene or diisopropylbenzene or to minimise any unwanted by-products.

Typically, under continuous flow conditions in the vapour phase benzene may be alkylated with ethylene at a temperature in the range from 200° to 500° C. preferably 300° to 450° C. and at a pressure which maintains the reactants in the vapour phase, preferably atmospheric to 25 bar. The molar ratio of benzene to ethylene may be in the range from about 0.1:1 to 100:1, preferably from 2:1 to 15:1. The ratio of catalyst volume to the gaseous feed volume flow rate (residence time) at NTP may be up to 2 minutes preferably in the range 0.1 to 60 seconds. The conditions may be permuted either to maximise desirable products such as ethyl benzene and diethyl-benzene or to minimise any unwanted by-products.

Typically, phenol may be alkylated at a temperature in the range from 50° to 300° C., preferably from 100° to 200° C., at atmospheric or elevated pressure. For example, phenol may be alkylated with high boiling olefins, eg hexene-1, at atmospheric pressure and at about 120° C. in a stirred glass vessel fitted with a reflux condenser. Using lower boiling olefins, eg ethylene and propylene, as the alkylating agent, elevated pressures may be employed to facilitate contact between the phenol and olefin reactants. Alternatively, there may be used other methods of mixing whereby the use of elevated pressure can be avoided, for example by bubbling the olefin through molten phenol containing the catalyst.

In a further aspect, the invention also provides a process for the production of an alcohol which process comprises reacting an olefin or olefin oxide with water at elevated temperature and pressure in the presence as catalyst of a stabilised pillared interlayered clay.

Suitably the olefin may be a lower olefin such as ethylene, propylene or a butylene, though higher olefins and mixtures of olefins may be employed if desired. Mixtures of olefins also comprise hydrocarbon fractions which contain substantial amounts of olefins, eg about 25 to about 90% by weight. Suitable olefin oxides which may be used include ethylene oxide and propylene oxide. Preferably the olefin is ethylene and the product produced by reaction with water in the presence of the catalyst is ethanol. In another preferred embodiment sec-butanol is produced by reacting linear butenes with water. In yet another preferred embodiment ethylene glycol is produced by reacting ethylene oxide with water.

In conducting the process of the invention the olefin or olefin oxide and water or steam may suitably be passed over the catalyst together at a reactant feed rate corresponding to a space velocity based on liquid reactants in the range of about 0.25 to 10 volumes of liquid feed per volume of catalyst per hour, ie about 0.25 to 10 L.H.S.V. The water to olefin mole ratio may be in the range of about 1:1 to 500:1 preferably from 5:1 to 400:1.

The total pressure in the reactor may range from about 50 psig to about 1500 psig and the temperature may be in the range from 50° to 400° C. The specific temperature chosen depends on the reactivity of the olefin or olefin oxide. The olefin oxides are the most reactive and a temperature in the range from about 40° to about 100°. C. is suitable. Propylene and the butenes are considerably more reactive than ethylene, and for the former olefins a temperature in the range of about 100° to about 240° C. is suitable. For ethylene the temperature may suitably be in the range from about 200° to 400° C. Since low temperatures are associated with high values of the equilibrium constant for alcohol formation, it is desirable to hydrate at the lowest temperature compatible with a reasonable rate of conversion.

The liquid phase reaction may be carried out in the presence of a solvent. A suitable solvent, for example, is ethyl carbitol.

The process may suitably be conducted in what is conventionally known as a "trickle bed" reactor, with at least a portion of the water in the liquid phase. Alternatively, the process may be operated in the gas phase.

In yet another aspect, the present invention provides a process for the production of an ester which process comprises reacting either an olefin or an olefin oxide with a carboxylic acid in the presence as catalyst of a stabilised pillared interlayered clay under reaction conditions which result in the formation of an ester.

With regard to the olefin or olefin oxide reactant any suitable olefin or olefin oxide may be employed. Suitable olefins include ethylene, propylene, butenes, pentenes and hexenes, diolefins such as butadiene and cyclic olefins such as cyclohexene. Mixtures of olefins such as those commonly encountered in petroleum refinery streams such as those obtained from the catalytic cracking of hydrocarbons, eg catcracked spirit, may also be used if so desired. Suitable olefin oxides include ethylene oxide and propylene oxide. The amount of olefin or olefin oxide employed may be greater or less than the stoichiometric amount required to react completely with the acid.

Both aromatic and aliphatic carboxylic acids may be used. Suitable aliphatic acids include formic, acetic, propionic and butyric acids. Of the aromatic acids phthalic acids, especially orthophthalic acid, may be employed. Mixtures of acids may also be employed if so desired.

Preferably the olefin is ethylene, the carboxylic acid is acetic acid and the ester produced is ethyl acetate. Ethylene glycol diacetate and 2-hydroxyethyl acetate can be obtained from the reaction of ethylene oxide and acetic acid.

The process may be carried out in the liquid phase or in the vapour phase, preferably in the liquid phase. Reaction conditions which result in the formation of an ester will depend on whether the process is carried out in the liquid or the vapour phase and to some extent on the nature of the reactants.

In the liquid phase the pressure is suitably any pressure which maintains a liquid phase at the reaction temperature. In the case of olefins and olefin oxides with suitably high boiling points, eg hexene-1, the reaction may for example be conveniently carried out at the reflux temperature of the reactants and under atmospheric pressure, or at higher temperatures and pressures if so desired. The temperature may suitably be in the range 20° to 300° C. In the case of ethylene, for example, the temperature may be in the range 100° to 300° C., preferably 150° to 250° C. Generally, using olefin oxides lower temperatures within the aforesaid range may be employed. In the case of propylene oxide, for example, the temperature may suitably be in the range 20° to 150° C., preferably 50° to 150° C. Solvents may be employed if desired. Suitable solvents include hydrocarbons, eg alkanes such as hexane and octane.

In the vapour phase the conditions must be chosen so that the reactants do not liquefy; for example in the production of ethyl acetate from ethylene and acetic acid, the acetic acid must be fed at atmospheric or slightly higher pressure otherwise it would liquefy at higher pressures. In the case of the reaction of ethylene and acetic acid, for example, the temperature may suitably be in the range 120° to 250° C., preferably 140° to 180° C. For the reaction of ethylene and acetic acid the residence time which is defined as:

$$\frac{\text{Volume of catalyst in mls}}{\text{Vapour flow rate (in mls/sec at } NTP)}$$

may suitably be in the range 10 to 60 secs, preferably 20 to 40 secs.

The process may be carried out batchwise or continuously, preferably continuously. The batchwise liquid phase production of ethyl acetate, for example, may conveniently be carried out by charging acetic acid and catalyst to an autoclave, pressurising the autoclave with ethylene, heating the autoclave to the desired reaction temperature and maintaining the autoclave at the reaction temperature. The reaction time should not be unduly protracted otherwise the selectivity for the conversion of acetic acid to ethyl acetate may be adversely affected. Thus at an approximately 2:1 molar ratio of ethylene to acetic acid, an initial ethylene pressure of 55 bar and a temperature of 200° C., the reaction time should preferably not exceed 5 hours. At the completion of the reaction the catalyst may be separated from the product, suitably by filtration, centrifugation or decantation and the reaction product worked up in known manner to recover ethyl acetate therefrom. The catalyst may thereafter be re-used in a further batch reaction with or without intervening treatment.

The invention will now be illustrated by reference to the following Examples.

All analytical results were determined using gas chromatography and the identity of the products was confirmed by comparison with authentic materials, mass spectroscopy or nuclear magnetic resonance spectroscopy.

In the Examples reference will be made to alumina pillared clay, hydrogen ion-exchanged clay and aluminium ion-exchanged pillared clay. These were prepared as follows:

PREPARATION 1

Preparation of Alumina Pillared Clay

Chlorhydrol (100 g, 50% w/w in water obtained from Armour Reheis) in 2 liters of distilled water was vigorously stirred whilst 100 g Wyoming bentonite powder was slowly added into the vortex of the solution. The pH of the mixture was adjusted to 5.0 by the addition of dilute ammonia solution. The mixture was then heated and stirred at 65° C. for 1 hour whilst maintaining the pH at 5.

On cooling, the clay was removed from solution by centrifuging and was washed with 3 liters of distilled water. The clay was then mixed with a further 3 liters of water, vigorously stirred for ½ hour and recentrifuged. The clay was oven dried at 80° C. and then heated at 500° C. for 2 hours. The basal $d_{001}$ spacing was 18.2 A.

PREPARATION 2

Preparation of Hydrogen Ion-Exchanged Pillared Clay 10 g of pillared clay, prepared as in Preparation 1, was placed in a dessicator over 20 ml of 0.91 ammonia solution and maintained at a 400 mbar pressure for 20 minutes. The clay was then added to a solution of 50 ml conc $H_2SO_4$ in 600 ml distilled water and left for 2 hours. The clay was then filtered off, washed with water to remove all extraneous ions, and oven dried at 80° C.

PREPARATION 3

Preparation of Aluminium Ion-Exchanged Pillared Clay

The procedure of Preparation 2 was followed except that the 50 ml conc $H_2SO_4$ was replaced by 60 g of aluminium sulphate $(Al_2(SO_4)_3 \cdot 16H_2O)$.

PREPARATION 4

Preparation of Hydrogen Ion-Exchanged Pillared Clay 10 g of pillared clay of 100 mesh, prepared as in Preparation 1, was added to 60 g of a 1M potassium hydroxide solution and left overnight at 80° C. The clay was filtered, washed in distilled water and refiltered to remove all extraneous ions, and added to 60 g of 1M sulphuric acid solution and left overnight. The hydrogen ion-exchanged pillared clay was filtered, washed in excess distilled water and refiltered to remove all extraneous ions and dried at 80° C. overnight.

PREPARATION 5

Preparation of Aluminium Ion-Exchanged Pillared Clay

Preparation 4 was repeated but using 1M aluminium chloride solution instead of 1M sulphuric acid solution.

EXAMPLE 1

5 g of alumina pillared clay, prepared as in Preparation 1, and 19 g methanol were sealed in a 100 ml stirred autoclave which was charged with 40 ml liquid but-1-ene and heated at 200° C. for 2.5 hours giving a maximum pressure of 80 bar. After cooling and venting, 16.1 g of liquid products were obtained which contained 19.9% wt of 2-methoxybutane as shown in Table 1.

EXAMPLE 2

Example 1 was repeated but using 5.0 g of hydrogen ion-exchanged alumina pillared clay as prepared in Preparation 2 instead of 5.0 g alumina pillared clay as prepared in Preparation 1. The result is shown in Table 1.

EXAMPLE 3

Example 1 was repeated using 5.0 g of aluminium ion-exchanged pillared clay as prepared in Preparation 3 instead of 5.0 g alumina pillared clay as prepared in Preparation 1. The result is shown in Table 1.

EXAMPLE 4

Example 1 was repeated using a reaction temperature of 175° C. instead of 200° C. and a maximum pressure of 60 bar instead of a maximum pressure of ca 80 bar. The result is shown in Table 1.

EXAMPLE 5

Example 4 was repeated using 5.0 g of hydrogen ion-exchanged pillared clay as prepared in Preparation 2 instead of the alumina pillared clay as prepared in Preparation 1. The result is shown in Table 1.

EXAMPLE 6

Example 4 was repeated using 5.0 g of aluminium ion-exchanged pillared clay as prepared in Preparation 3 instead of the alumina pillared clay as prepared in Preparation 1. The result is shown in Table 1.

EXAMPLE 7

Example 4 was repeated using 5.0 g of hydrogen ion-exchanged pillared clay as prepared in Preparation 4 instead of the alumina pillared clay as prepared in Preparation 1. The result is shown in Table 1.

EXAMPLE 8

Example 4 was repeated but using 5.0 g of aluminium ion-exchanged pillared clay, as prepared in Preparation 5, instead of the 5.0 g alumina pillared clay, prepared as in Preparation 1. The result is shown in Table 1.

TABLE 1

| Example No | Yield of 2-Methoxybutane in grams | Conversion of but-1-ene to 2-Methoxybutane |
| --- | --- | --- |
| 1 | 3.2 | 11.7 |
| 2 | 4.4 | 16.2 |
| 3 | 4.1 | 15.2 |
| 4 | 0.3 | 1.1 |
| 5 | 1.4 | 5.1 |
| 6 | 0.9 | 3.3 |
| 7 | 2.5 | 9.1 |

TABLE 1-continued

| Example No | Yield of 2-Methoxybutane in grams | Conversion of but-1-ene to 2-Methoxybutane |
| --- | --- | --- |
| 8 | 1.5 | 5.5 |

Examples 1 to 3 at 200° C. and 4 to 8 at 175° C. show that the yield of 2-methoxybutane is increased when the ion-exchanged pillared clays are used in place of the alumina pillared clay.

EXAMPLE 9

5 g of alumina pillared clay, prepared as in Preparation 1 and 19 g methanol were sealed in a 100 ml stirred autoclave which was charged with 40 ml liquid isobutene and heated at 80° C. for 2 hours giving a maximum pressure of less than 10 bar. After cooling and venting, 21.4 g of liquid products were obtained which contained 16.5% wt of methyl t-butyl ether (MTBE). The yield of MTBE was 3.5 g and the conversion of isobutene to MTBE was 12.9%.

EXAMPLE 10

A solution of ethanol and ethylene oxide (10.5:1 molar ratio) was passed over alumina pillared Wyoming bentonite (2–3.4 mm particle size) prepared as in Preparation 1, maintained at 119° C. and 20–22 bar pressure with a residence time of about 30 minutes. Essentially quantitative conversion of ethylene oxide to ethylene glycol ethers was obtained. The selectivity to ethylene glycol monoethyl ether was 90% w/w.

EXAMPLE 11

A suspension of ethanol (3 moles) and alumina pillared Wyoming bentonite (prepared as in Preparation 1) was maintained at 70° C. Ethylene oxide (0.3 moles) was added dropwise over a 2 h period. Essentially quantitative conversion of ethylene oxide to ethylene glycol ethers was obtained and the selectivity to ethylene glycol mono ethyl ether was 92% w/w.

EXAMPLE 12

A solution of ethanol and propylene oxide (9.7:1 molar ratio) was passed over alumina pillared Wyoming bentonite (2–3.4 mm particle size) prepared as in Preparation 1, maintained at 130°–132° C. and 20 bar pressure with a residence time of about 30 minutes. Essentially quantitative conversion of propylene oxide to propylene glycol ethers was obtained. The selectivity to propylene glycol mono-ethyl ether was 93% w/w.

EXAMPLE 13

A suspension of ethanol (3 moles) and alumina pillared Wyoming bentonite (prepared as in Preparation 1) was maintained at 75° C. Propylene oxide (0.3 moles) was added dropwise over a 2 h period. Essentially quantitative conversion of propylene oxide to propylene glycol ethers was obtained and the selectivity to propylene glycol mono ethyl ether was 96% w/w.

EXAMPLE 14

A suspension of hydrogen ion-exchanged pillared clay (prepared as in Preparation 2) in ethanol (2.17 moles) was stirred at 68° C. and atmospheric pressure. Propylene oxide (0.23 moles) was added dropwise over a 1 h period. Essentially quantitative conversion of propylene oxide to propylene glycol ethers was observed and the selectivity to propylene glycol monoethyl ether was 93.5% w/w.

EXAMPLE 15

A suspension of aluminium ion-exchanged pillared clay (prepared as in Preparation 3) in ethanol (2.17 moles) was stirred at 72° C. and atmospheric pressure. Propylene oxide (0.23 moles) was added dropwise over a 40 minute period. Essentially quantitative conversion of propylene oxide to propylene glycol ethers was observed and the selectivity to propylene glycol mono ethyl ether was 94% w/w.

EXAMPLE 16

A solution of butanol and ethylene oxide (10.0:1 mole ratio) was passed over alumina pillared clay (prepared as in Preparation 1) at 72° C. and atmospheric pressure with a residence time of about 30 minutes. A 92% w/w conversion of olefin oxide was obtained and the selectivity to ethylene glycol mono-butyl ether was 85% w/w.

EXAMPLE 17

A mixture of benzene and ethylene (molar ratio 7.4:1) were passed over alumina pillared clay (prepared as in Preparation 1, 2–3.4 mm particle size) maintained at 384° C. with a residence time at NTP of 10 seconds. 25.4% of the ethylene was converted to ethyl benzene. The major by-product was diethyl benzene and the ethyl benzene:diethyl benzene ratio was about 16:1 by weight. The selectivity for conversion of ethylene to ethyl benzene and diethyl benzene was 97.5%.

EXAMPLE 18

A mixture of benzene and ethylene (molar ratio of 8.3:1) were passed over alumina pillared clay (prepared as in Preparation 1, 2–3.4 mm particle size) maintained at 387° C. with a residence time at NTP of 36 seconds. 60% of the ethylene was converted to ethyl benzene. The major by-product was diethyl benzene and the ethyl benzene:diethyl benzene product ratio was about 20:1 by weight. The selectivity for conversion of ethylene to ethyl benzene and diethyl benzene was 87%.

EXAMPLE 19

5 g of alumina pillared clay (prepared as in Preparation 1) and 120 g benzene were sealed in a 150 ml stirred autoclave which was charged with 20 ml of liquid propene and heated at 230° C. for 2.5 hours giving a maximum pressure of 30 bar. After cooling and venting, 125 g of liquid products were obtained. The yield of cumene is shown in Table 2.

EXAMPLE 20

Example 19 was repeated but using 5.0 g of hydrogen ion-exchanged pillared clay (prepared as in Preparation 2) instead of the 5.0 g of alumina pillared clay (prepared as in Preparation 1). The yield of cumene is shown in Table 2.

EXAMPLE 21

Example 19 was repeated but using 5.0 g of aluminium ion-exchanged pillared clay (prepared as in Preparation 3) instead of the 5.0 g of alumina pillared clay (prepared as in Preparation 1). The yield of cumene is shown in Table 2.

TABLE 2

| Example No | Yield of cumene in grams |
|---|---|
| 19 | 20.8 |
| 20 | 24.7 |
| 21 | 23.9 |

Examples 19, 20 and 21 show that the yield of cumene is increased when the ion-exchanged pillared clays are used in place of the alumina pillared clay.

EXAMPLE 22

3.75 g alumina pillared clay (prepared as in Preparation 1) and 40 g water were sealed in a 100 ml stirred autoclave which was charged with 40 ml liquid but-1-ene and heated at 200° C. for 2.5 hours giving a maximum pressure of 60 bar. After cooling and venting, 39.4 g of liquid products were obtained which contained 3.3% wt of butan-2-ol. The yield of butan-2-ol was 1.30 g and the conversion of but-1-ene to butan-2-ol was 4.8%.

EXAMPLE 23

A stream of water and liquid mixed n-butenes in the molar ratio of 150:1 was passed over 40 ml alumina pillared clay (prepared as in Preparation 1) maintained at 212° C. and 50 bar pressure at the rate of 108 ml per hour. The aqueous products contained 0.5% w/w of butan-2-ol produced from butenes with a conversion of ca 15%.

EXAMPLE 24

3.75 g of alumina pillared clay (prepared as in Preparation 1) and 40 g water were sealed in a 100 ml stirred autoclave which was charged with 40 ml of liquid isobutene and heated at 100° C. for 2.5 hours giving a maximum pressure of 20 bar. After cooling and venting, the liquid products were removed and contained 0.21 g of tertiary butanol produced from isobutene with a conversion of ca 0.6%.

EXAMPLE 25

3.5 g of alumina pillared clay (prepared as in Preparation 1) and 30 g acetic acid were sealed in a 100 ml stirred autoclave which was charged with a 43 bar pressure of ethylene. The autoclave was heated at 200° C. for 2.5 hours giving a maximum pressure of 65 bar. After cooling and venting 28.3 g of liquid products were obtained which contained 1.1% wt of ethyl acetate. Acetic acid was converted to ethyl acetate at a selectivity of greater than 99%.

EXAMPLE 26

A suspension of hydrogen ion-exchanged pillared clay (prepared as in Preparation 4) in acetic acid (0.28 moles) was stirred at 60° C. and atmospheric pressure. Propylene oxide (0.28 moles) was added dropwise over a 40 minute period. Essentially quantitative conversion of propylene oxide was obtained. 2-Hydroxypropyl acetate (about 70% yield) was the major product.

We claim:

1. A method for carrying out a process capable of catalysis by protons using as catalyst a cation-exchangeable solid material characterised in that
the cation-exchangeable solid material is a stabilised pillared interlayed clay and wherein the process capable of catalysis by protons is a process for the production of an ester by reacting a olefin with a carboxylic acid.

2. A method according to claim 1 wherein the cation-exchangeable solid material clay is a cation-exchanged stabilised pillared interlayered clay.

3. A method according to claim 1 wherein the process capable of catalysis by protons is the production of ethyl acetate by reacting ethylene with acetic acid.

4. A method according to claim 1,
wherein said olefin is selected from the group consisting of ethylene, propylene, butenes, pentenes, and hexenes, and wherein said carboxylic acid is selected from the group consisting of formic acid, acetic acid, propionic acid and butyric acid.

5. A method according to claim 2 wherein the cation-exchangeable stabilised pillared interlayered clay is cation-exchanged with either hydrogen or aluminium ions.

* * * * *

UNITED STATES PATENT AND TRADEMARK OFFICE
CERTIFICATE OF CORRECTION

PATENT NO. : 4,665,220
DATED : May 12, 1987
INVENTOR(S) : REGINALD GREGORY et al

It is certified that error appears in the above-identified patent and that said Letters Patent is hereby corrected as shown below:

Col. 4, l. 24, there should be a hyphen between "2-ol"

Claim 1, col. 13, l. 3, before "olefin", change "a" to --an--.

Signed and Sealed this

Eighth Day of January, 1991

Attest:

HARRY F. MANBECK, JR.

*Attesting Officer*     *Commissioner of Patents and Trademarks*